United States Patent
Brockhoff

[11] Patent Number: 6,066,111
[45] Date of Patent: May 23, 2000

[54] METHOD OF BLOOD-GAS SEPARATION DEVICE AND SEPARATING DEVICE

[75] Inventor: Alexander Brockhoff, Furstentum, Liechtenstein

[73] Assignee: Convergenza AG, Liechtenstein

[21] Appl. No.: 08/934,941

[22] Filed: Sep. 22, 1997

[30] Foreign Application Priority Data

Dec. 5, 1996 [DE] Germany ............ 196 50 407

[51] Int. Cl.[7] ............ A61M 37/00; B01D 21/26
[52] U.S. Cl. ............ 604/5; 210/787
[58] Field of Search ............ 210/788, 787; 162/243, 245; 95/24; 604/73, 96, 4–6

[56] References Cited

U.S. PATENT DOCUMENTS

| | | |
|---|---|---|
| 2,511,967 | 6/1950 | Campbell ............ 183/82 |
| 2,876,860 | 3/1959 | Clark et al. ............ 183/2.5 |
| 3,715,863 | 2/1973 | Zanoni . |
| 3,753,336 | 8/1973 | Drew et al. . |
| 3,771,290 | 11/1973 | Stethem . |
| 3,785,380 | 1/1974 | Brumfield ............ 128/276 |
| 3,807,401 | 4/1974 | Riggle et al. . |
| 3,812,655 | 5/1974 | Bennett . |
| 3,833,013 | 9/1974 | Leonard . |
| 3,912,468 | 10/1975 | Tsuchiya et al. . |
| 3,955,573 | 5/1976 | Hansen . |
| 3,965,896 | 6/1976 | Swank . |
| 3,994,689 | 11/1976 | DeWall . |
| 3,996,027 | 12/1976 | Schnell et al. . |
| 4,053,291 | 10/1977 | Sims . |
| 4,054,522 | 10/1977 | Pinkerton . |
| 4,061,031 | 12/1977 | Grimsrud . |
| 4,093,428 | 6/1978 | Swogger . |
| 4,102,655 | 7/1978 | Jeffery et al. . |
| 4,247,309 | 1/1981 | Buddenhagen . |
| 4,282,016 | 8/1981 | Tauber et al. . |
| 4,316,271 | 2/1982 | Evert . |
| 4,344,777 | 8/1982 | Siposs . |

(List continued on next page.)

FOREIGN PATENT DOCUMENTS

| | | |
|---|---|---|
| 318 993 | 6/1989 | European Pat. Off. . |
| 778 031 | 6/1997 | European Pat. Off. . |
| 26 11 383 | 9/1977 | Germany . |
| 1526509 | 9/1978 | Germany . |
| 3011681 | 10/1980 | Germany . |
| 43 26 886 | 2/1995 | Germany . |
| 43 29 385 | 3/1995 | Germany . |
| 4326886 | 8/1995 | Germany . |
| 195 45 404 | 6/1997 | Germany . |
| 2063108 | 6/1981 | United Kingdom . |
| 92 20380 | 11/1992 | WIPO . |

*Primary Examiner*—John G. Weiss
*Assistant Examiner*—Patricia Bianco
*Attorney, Agent, or Firm*—Beck & Tysver PLLC

[57] ABSTRACT

The invention concerns a method and apparatus for removing gas from blood, comprising drawing blood through a non-rotating centrifuge chamber, the chamber having an inlet above and an outlet below with the chamber narrowing like a funnel between the inlet and the outlet. The inlet is oriented for directing the flow tangentially into the blood inlet and around the centrifuge chamber. The outlet is connected to a suction source for drawing off blood without reversal of the direction of rotation of the stream of blood in the chamber. The blood is further directed in the direction of flow of blood obliquely downward into the centrifuge chamber with an upwardly open angle to the axis rotation that is less than 90°. An additional chamber communicates with the centrifuge chamber above the blood inlet and defines a gas base that is larger in cross-section than the gas outlet for providing a gas base for separation of the gas and blood. There is a gas outlet located at a vertical elevation that is higher than the blood inlet for the centrifuge chamber and that communicates with the blood inlet for drawing gas off from the surface of the stream of blood that is rotating in the centrifuge chamber. The apparatus includes a handgrip enabling single hand holding. The centrifuge chamber may be in the handgrip. A blood suction tube may carry blood from a site to the blood inlet.

18 Claims, 4 Drawing Sheets

6,066,111

U.S. PATENT DOCUMENTS

| | | |
|---|---|---|
| 4,345,919 | 8/1982 | Wilkinson et al. . |
| 4,360,428 | 11/1982 | Comparetto et al. . |
| 4,368,118 | 1/1983 | Siposs . |
| 4,388,922 | 6/1983 | Telang . |
| 4,390,048 | 6/1983 | Zelder ........................................ 141/6 |
| 4,394,138 | 7/1983 | Schilling . |
| 4,433,971 | 2/1984 | Lindsay et al. . |
| 4,474,184 | 10/1984 | Harui . |
| 4,475,932 | 10/1984 | Hull et al. . |
| 4,555,253 | 11/1985 | Hull et al. . |
| 4,585,465 | 4/1986 | Suzuki et al. . |
| 4,690,762 | 9/1987 | Katsura . |
| 4,710,299 | 12/1987 | Pendergast . |
| 4,749,387 | 6/1988 | Lotz . |
| 4,806,135 | 2/1989 | Siposs . |
| 4,860,591 | 8/1989 | Garland . |
| 4,874,359 | 10/1989 | White et al. . |
| 4,900,308 | 2/1990 | Verkaart . |
| 4,919,826 | 4/1990 | Alzner ........................................ 210/788 |
| 4,940,473 | 7/1990 | Benham . |
| 4,966,703 | 10/1990 | Kalnins et al. . |
| 4,976,685 | 12/1990 | Block, Jr. .................................. 604/52 |
| 4,997,556 | 3/1991 | Yano et al. ................................ 210/136 |
| 5,000,766 | 3/1991 | Yano et al. ................................ 55/204 |
| 5,061,236 | 10/1991 | Sutherland et al. . |
| 5,064,449 | 11/1991 | Ford et al. ................................. 55/52 |
| 5,152,964 | 10/1992 | Leonard . |
| 5,171,405 | 12/1992 | Torregrossa ............................... 162/243 |
| 5,188,604 | 2/1993 | Orth . |
| 5,228,889 | 7/1993 | Cortial et al. . |
| 5,386,734 | 2/1995 | Pusinelli . |
| 5,411,472 | 5/1995 | Steg, Jr. et al. ............................. 604/4 |
| 5,429,595 | 7/1995 | Wright, Jr. et al. . |
| 5,451,321 | 9/1995 | Matkovich . |
| 5,453,196 | 9/1995 | Tuszko et al. .......................... 210/512.1 |
| 5,486,162 | 1/1996 | Brumbach . |
| 5,503,801 | 4/1996 | Brugger . |
| 5,531,119 | 7/1996 | Meyers . |
| 5,537,335 | 7/1996 | Antaki et al. . |
| 5,582,633 | 12/1996 | Jiang et al. . |
| 5,591,251 | 1/1997 | Brugger . |
| 5,622,545 | 4/1997 | Mazzei et al. ............................. 96/210 |
| 5,632,894 | 5/1997 | White et al. . |
| 5,674,199 | 10/1997 | Brugger . |
| 5,707,431 | 1/1998 | Verkaart et al. ........................... 96/177 |
| 5,755,965 | 5/1998 | Reiber . |
| 5,824,212 | 10/1998 | Brockhoff ................................. 210/194 |
| 5,861,052 | 1/1999 | Meinander ................................ 95/243 |

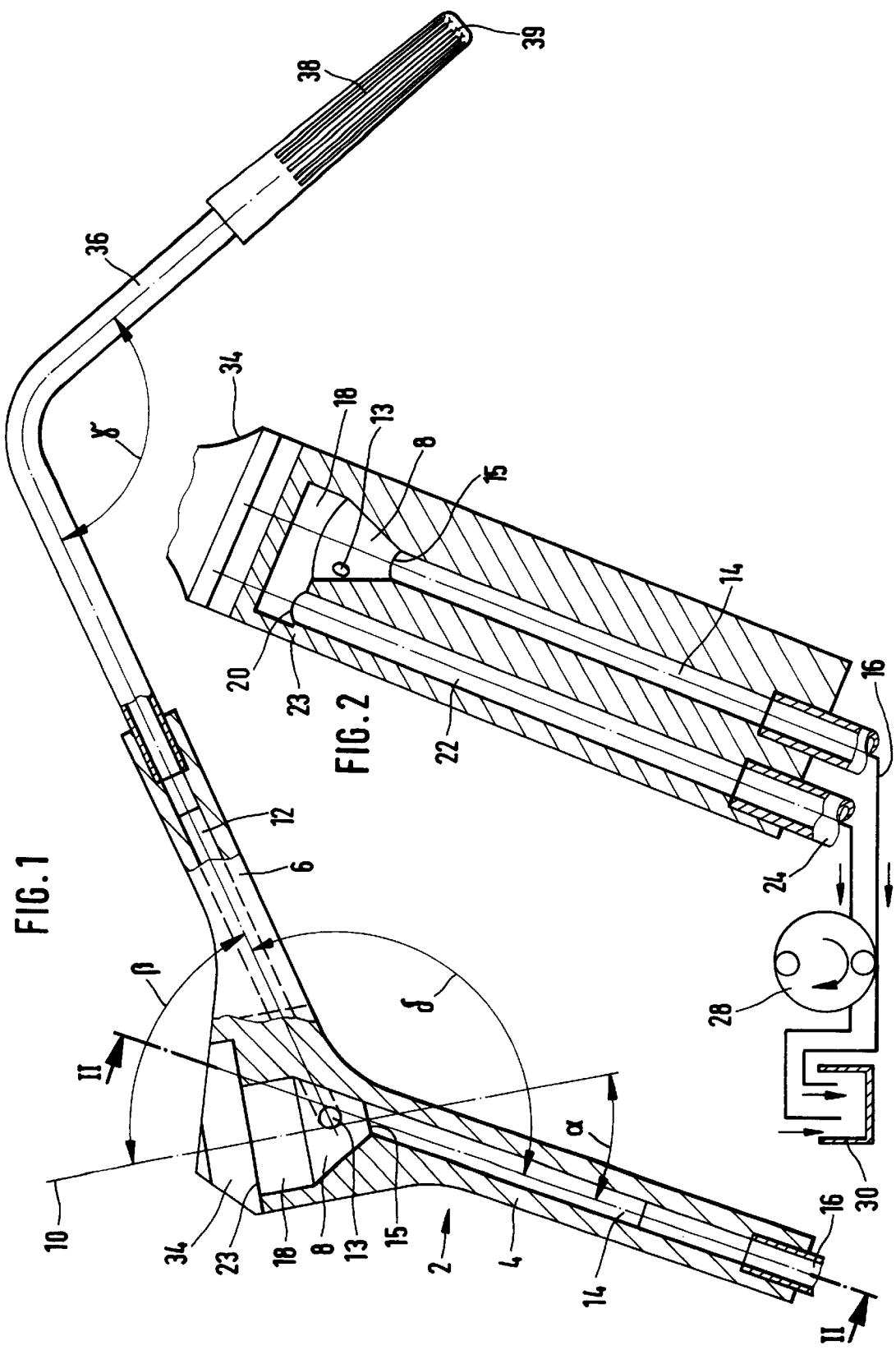

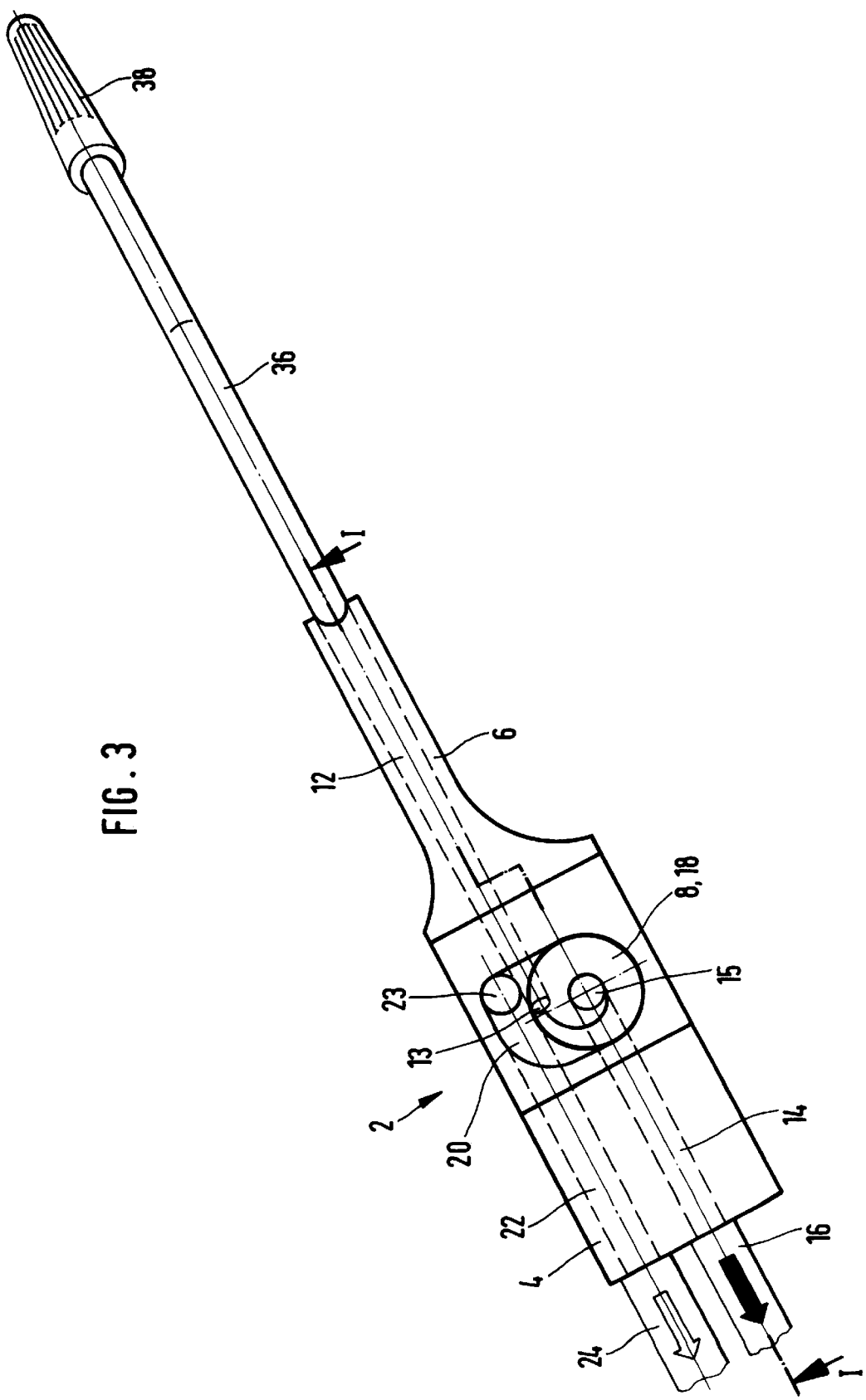

METHOD OF BLOOD-GAS SEPARATION DEVICE AND SEPARATING DEVICE

BACKGROUND OF THE INVENTION

The present invention relates to a method and an apparatus for separating blood and gas and particularly to moving blood through a non-rotating centrifuge for separating blood and gas.

It is useful medical procedure to draw blood from the site of a patient's wound and then introduce the drawn blood back into the patient or into another patient. The wound may be due to surgery or accident. As blood is withdrawn, it is common for air to inadvertently be introduced into the blood at the site of the withdrawal. However, blood that contains air must under no circumstances be admninistered to a patient. Therefore, air must be separated from the blood before it is introduced or re-introduced into a patient. Furthermore, blood is damaged by inclusions of air the longer the drawn-in air remains in the blood. Still further, blood is damaged the more that air is mixed with blood within the blood-removal path. Therefore, it is desirable to separate the air from the blood as close as possible to the site of the removal or withdrawal from the patient.

The quality of blood can be impaired among other things by the amount and length of presence of air or other gases in the blood; by suction or pressure forces on the blood; by frictional forces of the blood in flow paths, and by deflections of the flow of blood and turbulence in the blood.

There are several situations in which gas must be separated from blood. Each situation presents its own set of conditions which must be accommodated by the methods and apparatus used to separate the gas and blood.

In a first case of use, blood is degasified while it is drawn in relatively small and strongly varying amounts from a patient, in particular through a suction tube from the site of a wound which may have been caused by an accident or an operation. Vacuum for drawing the blood is produced by a suction pump, generally a roller pump. The suction pump not only draws off blood but frequently also draws off air at the place where blood is being removed from the patient. The amount of air which is drawn off is relatively large, as compared with the amount of blood being drawn off, for instance five parts of air to one part of blood (parts by volume). The blood-removal rate is relatively low, for example 100 to 600 milliliters per minute, and it varies greatly. The suction flow speed of the blood is also relatively low and varies greatly.

The air bubbles contained in the blood are frequently relatively large. Their size ranges from the micrometer range to the millimeter range. The present invention concerns this first case of use, namely degasifying blood while it is being drawn off from a patient.

The second case of use concerns administering blood to a patient, for instance upon dialysis or after a large loss of blood in an accident. Blood which is administered to a patient cannot be fed by suction but can only be administered to the patient by the pressure of a pressure pump. The blood rate, for instance three liters per minute, and the speed of conveyance of the blood are relatively high and substantially constant. The amount of air in the blood is, however, slight, for instance only $50 \times 10^{-6}$ parts by volume of air to one part by volume of blood. The air has the form of only very small bubbles in the micrometer range.

The third case of use concerns the handling of blood outside a patient and independently of the patient. Here, similar to the second case, there are substantially constant blood flow quantities and constant speeds of flow of blood.

For the first case of use, U.S. Pat. No. 3,785,380 discloses a blood removal device which consists of a cylindrical housing in which microporous filter material is present for filtering air bubbles and other impurities out of a stream of blood drawn off from a patient, a blood suction tube at a front end of the housing, and a blood suction line at the rear end of the housing.

Literature concerning the second case of use includes GB-A-2 063 108 which shows a blood degasification device for removing bubbles of gas which can be so small as to lie in the micro range, for instance having a diameter of only 40 microns. This blood suction device has a vertically arranged cylindrical cyclone chamber, with a tangential inlet at the upper end of the chamber, and a blood outlet at the lower end of the chamber arranged tangentially opposite the direction of rotation of the cyclone. An air vent tube extends in downward direction in the axis of rotation of the cyclone to a level below the blood inlet into the cyclone chamber. A second venting means is in the form of a radial hole in an upper extension of the cyclone chamber above the blood inlet. A second tube extends through the entire cyclone chamber along the axis of rotation of the cyclone and through a part of the first mentioned tube. The second tube serves so that air bubbles collect on its outer surface and can rise upward. German DE-A-43 29 385 describes an air separator which is an improvement on the one described in the above described GB-A-2 063 108. In the German publication, the blood inlet and blood outlet are arranged axially to each other at the ends of a cylindrical eddy chamber which face each other. The blood inlet is formed by a guide blade body and there is a filter candle in front of the blood outlet. Ascending bubbles of blood enter into a section of the eddy chamber which is located above the guide blade body and in which an air cushion is formed which is vented by a hole. German DE-C-36 41 644 shows a blood flow chamber having a blood inlet at the mid-height of the chamber and a blood outlet channel immersed in the flow chamber. Air bubbles contained in the blood can rise upward only due to the Archimedean buoyancy force.

Furthermore, German DE-C-36 24 363 and U.S. Pat. No. 5,451,321 show devices with microporous filter material for filtering gas bubbles or other blood impurities out of a stream of blood.

SUMMARY OF THE INVENTION

The object of the present invention is to provide a method and an apparatus for drawing off blood from a patient such that a weak suction or vacuum is obtained, even for small and varying amounts of flow of blood, in order to draw the blood through a non-rotating centrifuge chamber or cyclone chamber to obtain a good and rapid separation of blood and gas, particularly air, mixed with the blood.

The invention concerns a method and apparatus for removing gas from blood, comprising drawing blood through a non-rotating centrifuge chamber, the chamber having an inlet above and an outlet below with the chamber narrowing like a funnel between the inlet and the outlet. The inlet is oriented for directing the flow tangentially into the blood inlet and around the centrifuge chamber. The outlet is connected to a suction source for drawing off blood without reversal of the direction of rotation of the stream of blood in the chamber. The rotation of the stream of blood in the chamber. A blood inlet suction channel in the shaft discharges at a blood inlet opening located approximately tangentially and obliquely downward at an angle of preferably 90 degrees or less to the vertical axis of rotation.

An additional chamber communicates with the centrifuge chamber above the blood inlet and defines a gas base that is larger in cross-section than the gas outlet for providing a gas space for separation of the gas and blood. There is a gas outlet located at a vertical elevation that is higher than the blood inlet for the centrifuge chamber and that communicates with the blood inlet for drawing gas off from the surface of the stream of blood that is rotating in the centrifuge chamber. The apparatus includes a handgrip enabling single hand holding. The centrifuge chamber may be in the handgrip. A blood suction tube may carry blood from a site to the blood inlet.

The invention has several advantages. For removing gas bubbles of all sizes, the invention employs the centrifugal forces of a cyclone flow, with the gas removal suction action from above on the rotating blood, and the Archimedean buoyancy forces simultaneously and in a manner supporting each other, as described in greater detail below in conjunction with the detailed description of the invention. As a result, even with only weak suction by a suction pump, gentle and effective separation of the gas phase from the blood phase takes place. The non-rotating centrifuge chamber or cyclone chamber is funnel shaped and narrows in the downward direction from the blood inlet to the blood outlet below the inlet so that the centrifugal kinetic energy of the cyclone flow from the blood inlet to the blood outlet is maintained better than with a non-funnel-shaped cylindrical chamber. In accordance with the invention, even with small quantities and small speeds of blood flow, rotation of the blood is still produced with sufficient centrifugal force for removing air from the blood, even with weak suction by the suction pump.

Effectiveness is further improved because the blood inlet channel is not only approximately tangential to but is directed in the direction of the flow of blood also obliquely downward into the cyclone chamber. This causes even small drop-like amounts of blood in the chamber to be rotated by the suction of the blood suction pump and to be freed of air bubbles.

Better separation of blood and gas from the stream of blood is obtained by means of a gas space located above the rotating stream of blood. Bubbles and blood-gas foam have sufficient time and space in the gas space to break down into an air portion and a blood portion before the gas is drawn off by a gas suction device at a distance above the rotating stream of blood. The invention is used preferably for the above indicated first case in the blood suction stream of a patient. However, the invention can also be used for the third case of use for effectively removing gas from blood and-may be employed independently of a patient because blood is drawn from a blood container through the centrifuge chamber or cyclone chamber. The apparatus can be arranged close to a patient. It is very light in weight. It can be developed as a portable single hand operated device. It can be manufactured economically with the use of commercially available tubes. It is simple to handle and is not tiring for the operator to use.

Other features and advantages of the present invention will become apparent from the following description of the invention which refers to the accompanying drawings.

BRIEF DESCRIPTION OF THE DRAWINGS

FIG. 1 is a side view, partially along the plane I—I of FIG. 3, of a blood suction device according to the invention;

FIG. 2 is a diagrammatic longitudinal section along the plane II—II of FIG. 1;

FIG. 3 is a top view of the blood suction device of FIG. 1;

DETAILED DESCRIPTION OF THE INVENTION

Figure 4:
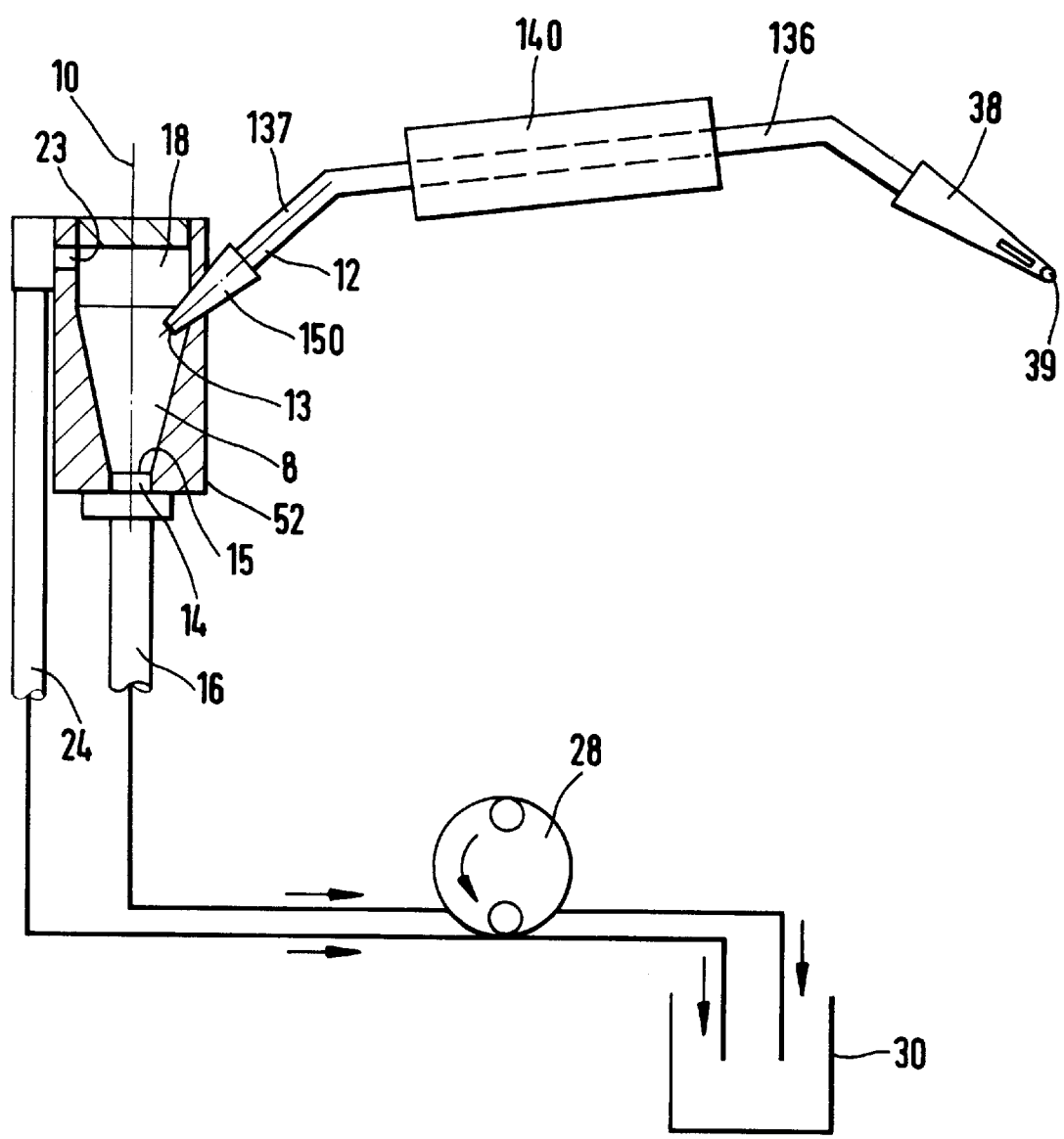
FIG. 4 is a side view, partially in section, of another embodiment of the invention.

The embodiment of a blood suction device of the invention for drawing blood from a patient, particularly from a wound site of a patient, which is shown in FIGS. 1 to 3, is a single hand held and operated device. It contains a single piece or multi-piece pistol shaped body 2 of metal or plastic which is comprised of a grip 4 and a barrel or shaft 6.

In the crossing region of the body 2, between grip 4 and shaft 6, there is a non-rotating centrifuge chamber, also referred to as a cyclone chamber 8, for producing a stream of blood which rotates in cyclone-like manner with constant direction of rotation around an upright, vertical or approximately vertical axis of rotation 10. The cyclone chamber 8 has a shape which narrows like a funnel downward from its top to its bottom so that a stream of blood drawn down through the chamber 8 substantially retains its kinetic energy throughout the entire cyclone chamber without a strong suction force being necessary in the cyclone chamber.

A blood inlet suction channel 12 in the shaft 6 dischanges at a blood inlet opening 13 located approximately tangentially and obliquely downward at an angle $\beta$ of 90°, or preferably less than 90°, to the vertical axis of rotation 10 and opens into the funnel shaped upper section of the funnel shaped cyclone chamber 8.

A blood outlet suction channel 14 extends from a blood outlet opening 15 at the narrow lower end of the cyclone chamber 8 at a downwardly open angle $\alpha$ of between 0° and 90°, and preferably about 30°, to the axis of rotation 10 through the grip 4 to a blood suction hose 16 which is connected to the lower end of the channel 14. In this way, the blood outlet suction channel 14 extends either axially to the axis of rotation 10 or obliquely from the top front to the bottom rear away from it. On the flow path between the blood inlet suction channel 12 and the blood outlet suction channel 14, the stream of blood rotates, without reverse flows, in only a single direction of eddy rotation.

The cyclone chamber 8 is elongated upward approximately 5 mm to 15 mm in height by a closed gas space 18 arranged at its top. The gas space has a gas space section 20 that protrudes laterally beyond the cyclone chamber 8. The gas space 18 serves as a storage chamber for temporarily receiving gas bubbles and blood foam so that they have time and space to break down and separate into air and blood. In this way, the blood portion which is drawn off, separated from the rotating stream of blood, with the gas is reduced. The gas space 18 also serves for temporarily receiving blood which may at times rise from the cyclone chamber 8. The cross section of the gas space 18 transverse to the axis of rotation 10 is at least twice as great as the cross section of a gas outlet opening 23.

A gas outlet suction channel 22 extends through the grip 4, parallel to the blood outlet suction channel 14. It is connected via the gas outlet opening 23 in the bottom of the laterally protruding section 20 to the gas space 18. The gas outlet opening 23 is arranged substantially higher, for instance 2 mm to 10 mm higher, than the blood inlet opening 13. A gas removal hose 24 is connected to the gas outlet suction channel 22 at the lower end of the grip 4. The gas suction hose 24 and the blood suction hose 16 are connected separately to a suction pump 28, preferably a peristaltic roller pump, which conveys the blood and the air drawn off on separate paths into a blood reservoir 30. Acting through the blood outlet suction-channel 14 and the gas outlet suction channel 22 and then through the gas space 18 and the cyclone chamber 8, the suction pump 28 produces a suction vacuum in the blood inlet suction channel 12 so that blood is drawn into the cyclone chamber 8 through the blood inlet suction channel 12.

The gas space 18 is closed by a cover 34.

A blood suction tube 36 can be detachably inserted into the distal (front) end of the blood inlet suction channel 6. In another embodiment, the blood suction tube 36 may also be in one piece with the body 2 of the device. The front end section of the blood suction tube 36 is bent downward by a downwardly open angle γ of, for instance, 105°. It also has passage openings 39 along it to enable blood to be drawn from the wound site of the patient when an operator holds the body 2 of the device by the grip 4 in a convenient position of his hand. Accordingly, the angle γ of the blood suction tube 36 can be within the range of 90° and 180°.

The grip 4 and, within it, the parallel blood outlet suction channel 14 and gas outlet suction channel 22 all extend obliquely downward to the rear at a downwardly open angle α of between 0° and 90°, and preferably approximately 30°, relative to the cyclone axis of rotation 10. The angles α and γ are so adapted to each other that, upon the drawing off of blood, the apparatus can be held conveniently by the grip and in this connection the gas outlet opening 23 always remains at a higher elevation than the blood inlet opening 13. Therefore, the gas outlet opening 23 is preferably arranged on the side of the chamber facing away from the blood inlet opening 13.

The downwardly open angle δ between the blood outlet suction channel 14 and the gas outlet suction channel 22, on the one hand, and the blood inlet suction channel 12, on the other hand, is, depending on the angles α and β, between about 90° and 180° and preferably, in the preferred embodiment shown, 135°.

In the preferred embodiment, the gas outlet suction channel 22 and its gas suction hose 24 have an inner cross section that is either the same as or different from the blood suction channel 14 and its blood suction hose 16 so that blood and air can be drawn off separately from each other by the same suction pump 28, even if the blood and the air have different volumes of flow.

The conical or funnel shape of the cyclone chamber 8, which narrows in the downward direction from the vicinity of the blood inlet opening 13 to the vicinity of the blood outlet opening 15, assures that the energy of rotation of the stream of blood is maintained without substantial loss from the blood inlet suction channel 12 up to the blood outlet suction channel 14, even if only a slight suction, which acts gently on the blood, is produced at the blood outlet 15 by the suction pump 28.

If the downstream end section of the blood inlet suction channel 12 at the blood inlet opening 13 is directed not only essentially tangentially but also obliquely downward at an angle β of less than 90° into the cyclone chamber 18 and is thus inclined in the direction of the suction in the blood outlet suction channel 14, then even small drop-like amounts of blood are rotated so rapidly by this suction in the cyclone chamber 18 that centrifugal forces are produced which separate blood and air.

In the embodiment of the invention shown in FIG. 4, a commercial blood suction tube 136 having a hand grip part 140 is used. The downstream, rear end section 137 of the blood suction tube 136 forms, directly or by a connecting piece 150, the blood inlet suction channel 12 with the blood inlet opening 13 in the cyclone chamber 8. The cyclone chamber 8 and the upwardly extending gas space 18 which adjoins it at its upper end are formed in a housing 52. The other details which are shown in FIG. 4 are structurally and at least functionally identical to the views of FIGS. 1 to 3 and are provided with the same reference numerals.

Figure 5:
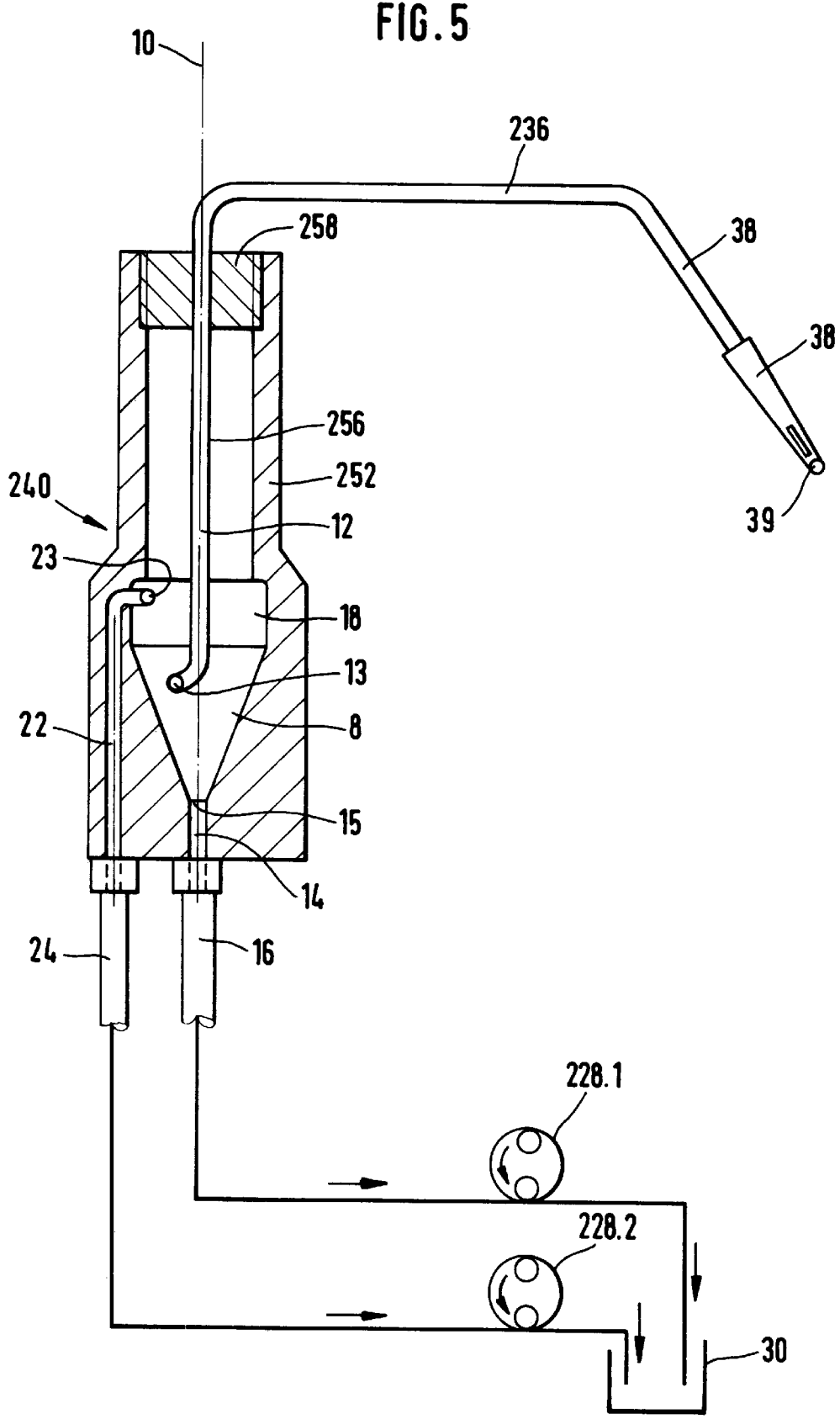
FIG. 5 is a side view, partially in section, of still another embodiment of the invention.

In the further embodiment of the invention shown in FIG. 5, the cyclone chamber 8 and the gas space 18 are formed in a housing 252 which is also developed as a hand grip part 240. This enables the entire device to be carried in one hand. The blood suction tube 236 is provided on its downstream rear end with a length of tube 256 that extends vertically from above and into the housing 252. It forms the blood inlet suction channel 12 and, at its downstream end, it forms the blood inlet opening 13. The gas space 18 is closed at its top by a closure 258 at the upper end of the housing 252. A suction pump 228.1 for the blood and a separate suction pump 228.2 for the gas are provided. But the two pumps can be replaced by a single pump 28 in accordance with FIGS. 1 to 4. The vacuum generated by these pumps produces, through the gas outlet opening 23, the blood outlet opening 15, the cyclone chamber 18 and the blood suction tube 236, a vacuum or suction which draws blood from the wound site of a patient and into openings 39 on the front end of the catheter. The further parts of the embodiment of FIG. 5 are the same as in the embodiment of FIGS. 1 to 3 and are provided with the same reference numerals.

In FIGS. 4 and 5, the blood outlet suction channels 14 are aligned with the vertical axis of rotation 10 of the cyclone chamber 8, which acts as a centrifuge chamber.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. Apparatus for removing gas from blood comprising:
   a non-rotating centrifuge chamber having a shape which narrows in a tapering funnel manner from an upper portion above to a lower portion below, the chamber having a blood inlet to the wider top end and a blood outlet from the narrower lower end in order to reduce the loss of energy of rotation of a blood stream that is sucked through the chamber;
   the blood inlet to the chamber being oriented to be substantially tangential to the axis of rotation of the stream of blood in the centrifuge chamber to form a stream of blood rotating around the substantially vertical axis of rotation of the centrifuge chamber, the blood inlet into the chamber being further directed in the direction of the flow of blood obliquely downward into the centrifuge chamber with an upwardly open angle β to the axis of rotation of less than 90°;
   the blood outlet being connectable to a suction device for drawing blood through the centrifuge chamber from the inlet to the outlet without reversal of direction of rotation of the stream of blood in the chamber;
   a gas outlet located at a vertical elevation higher than the blood inlet to the centrifuge chamber and communicating with the blood inlet for drawing gas off from the surface of the stream of blood that is rotating in the centrifuge chamber, and the gas outlet being connectable to a suction device which enables the gas to be drawn off the surface of the stream of blood and through the gas outlet through a suction device;

said apparatus being shaped so as to be gripped and carried with one hand.

2. The apparatus of claim 1, wherein the handgrip is sized so that the centrifuge chamber is arranged at the upper end of the handgrip.

3. The apparatus of claim 1, wherein the centrifuge chamber is arranged at the rear or lower end with respect to the direction of blood flow, downstream of the handgrip.

4. The apparatus of claim 1, wherein the centrifuge chamber is integrated into the handgrip.

5. The apparatus of claim 1, further comprising a blood suction tube connected to the blood inlet for bringing blood from a source to the blood inlet, the handgrip being provided on the blood suction tube.

6. The apparatus of claim 1, wherein the blood outlet is of a different cross-sectional size than the air outlet.

7. The use of the apparatus of claim 1, by placing the blood suction tube at a wound site of a patient.

8. Apparatus for removing gas from blood comprising:
a non-rotating centrifuge chamber having a shape which narrows in a tapering funnel manner from an upper portion above to a lower portion below, the chamber having a blood inlet to the wider top end and a blood outlet from the narrower lower end in order to reduce the loss of energy of rotation of a blood stream that is sucked through the chamber;
the blood inlet suction channel to the chamber being oriented to be substantially tangential to the axis of rotation of the stream of blood in the centrifuge chamber to form a stream of blood rotating around the substantially vertical axis of rotation of the centrifuge chamber, the blood inlet into the chamber being further directed in the direction of the flow of blood obliquely downward into the centrifuge chamber with an upwardly open angle $\beta$ to the axis of rotation of less than 90°;
the blood outlet being connectable to a suction device for drawing blood through the centrifuge chamber from the inlet to the outlet without reversal of direction of rotation of the stream of blood in the chamber;
a gas outlet located at a vertical elevation higher than the blood inlet to the centrifuge chamber and communicating with the blood inlet for drawing gas off from the surface of the stream of blood that is rotating in the centrifuge chamber, and the gas outlet being connectable to a suction device which enables the gas to be drawn off the surface of the stream of blood and through the gas outlet through a suction device; said gas outlet connected to a gas outlet suction channel;
an additional gas extraction chamber communicating with the centrifuge chamber above the blood inlet and defining a gas space communicating with the gas outlet, the additional chamber having a cross-section in the direction transverse to the axis of rotation which is at least twice as great as the cross-section of the gas outlet for providing the gas bubbles and blood-gas foam time and space in the gas space to break down into blood parts and gas parts before the gas parts may be drawn off through the gas outlet by a vacuum source connected thereto;
a blood suction tube connected to the blood inlet suction channel for bringing blood from a source through the blood inlet; said blood suction tube forming an angle with said blood suction channel;
said apparatus being shaped so as to be gripped and carried with one hand and having said blood outlet channel housing forming a handgrip for holding and gripping said apparatus.

9. An apparatus according to claim 8, wherein said angle defined between the blood suction tube and the blood inlet suction channel is between about 90° and 180°.

10. An apparatus according to claim 9, wherein the blood outlet suction channel and gas outlet suction channel each extend obliquely downward away from said cyclone chamber at a downwardly open angle $\alpha$ of between about 0° and 90° relative to the cyclone axis of rotation.

11. An apparatus according to claim 8, wherein the blood outlet suction channel and gas outlet suction channel extend obliquely downward to the rear at a downwardly open angle $\alpha$ of between about 0° and 90° relative to the cyclone axis of rotation.

12. An apparatus according to claim 8, wherein the handgrip is sized so that the centrifuge chamber is arranged at the upper end of the handgrip.

13. An apparatus according to claim 8, wherein the centrifuge chamber is arranged at the rear or lower end with respect to the direction of blood flow, downstream of the handgrip.

14. An apparatus according to claim 8, wherein the centrifuge chamber is integrated into the handgrip.

15. A method of removing gas from blood comprising the steps of:
a) providing a liquid and gas separating device having:
i) a blood suction tube,
ii) a cyclone chamber for dynamically separating liquid and gas, said cyclone chamber in fluid communication with said blood suction tube and downstream of said blood suction tube; said cyclone chamber in communication with a gas extraction chamber;
iii) a gas outlet in fluid communication with said gas extraction chamber;
iv) a liquid outlet in fluid communication with said cyclone chamber;
v) a suction device pump in fluid communication with said gas outlet and said liquid outlet;
b) placing the blood suction tube at a patient's wound site;
c) operating said suction device pump to draw blood from the patient into the cyclone chamber;
d) separating the gas phase from the liquid phase in said cyclone chamber;
e) operating said suction device to draw the gas phase and the liquid phase from said respective outlets, said suction device drawing said gas and said liquid phases separately.

16. A method of removing gas from blood according to claim 15 wherein in step e), the suction device pump draws gas and liquid phases in equal volumes.

17. A method of removing gas from blood according to claim 15 wherein in step e), the suction device draws gas and liquid phases in differing volumes.

18. An apparatus for removing gas from blood, comprising:
a) a blood suction tube for insertion into blood and coupled to said cyclone chamber;
b) a cyclone chamber for dynamically separating liquid and gas, said chamber in fluid communication with said blood suction tube through a blood inlet and said cyclone chamber being downstream of said blood suction tube; said cyclone chamber in communication with a gas extraction chamber;
c) a gas outlet in fluid communication with said gas extraction chamber;
d) a liquid outlet in fluid communication with said separation chamber and offset with respect to; and
a suction device pump located downstream of said separation chamber and in fluid communication with said gas outlet and said liquid outlet.

* * * * *